US009629907B2

(12) United States Patent
Weiner et al.

(10) Patent No.: US 9,629,907 B2
(45) Date of Patent: Apr. 25, 2017

(54) COMPOSITIONS FOR AND METHODS OF INDUCING MUCOSAL IMMUNE RESPONSES

(75) Inventors: David B Weiner, Merion, PA (US); Michele Kutzler, Souderton, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/284,824

(22) Filed: Oct. 28, 2011

(65) Prior Publication Data

US 2012/0195928 A1 Aug. 2, 2012

Related U.S. Application Data

(62) Division of application No. 11/719,646, filed as application No. PCT/US2005/042231 on Nov. 18, 2005, now abandoned.

(60) Provisional application No. 60/629,737, filed on Nov. 19, 2004, provisional application No. 60/647,617, filed on Jan. 27, 2005.

(51) Int. Cl.
| | | |
|---|---|---|
| A61K 39/39 | (2006.01) | |
| A61K 39/12 | (2006.01) | |
| A61K 39/21 | (2006.01) | |
| C07K 14/005 | (2006.01) | |
| A61K 39/00 | (2006.01) | |

(52) U.S. Cl.
CPC ............. *A61K 39/39* (2013.01); *A61K 39/12* (2013.01); *A61K 39/21* (2013.01); *C07K 14/005* (2013.01); *A61K 2039/53* (2013.01); *A61K 2039/541* (2013.01); *A61K 2039/55516* (2013.01); *C12N 2740/16222* (2013.01); *C12N 2740/16234* (2013.01)

(58) Field of Classification Search
None
See application file for complete search history.

(56) References Cited

U.S. PATENT DOCUMENTS

| | | |
|---|---|---|
| 4,510,245 A | 4/1985 | Cousens et al. |
| 4,722,848 A | 2/1988 | Paoletti et al. |
| 4,790,987 A | 12/1988 | Compans et al. |
| 4,797,368 A | 1/1989 | Carter et al. |
| 4,845,050 A | 7/1989 | Kim et al. |
| 4,920,209 A | 4/1990 | Davis et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III et al. |
| 5,389,368 A | 2/1995 | Curtiss, III |
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,972 A | 4/1998 | Smith et al. |
| 5,817,637 A | 10/1998 | Weiner et al. |
| 5,830,876 A | 11/1998 | Weiner et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |
| 6,156,319 A | 12/2000 | Cohen et al. |

(Continued)

FOREIGN PATENT DOCUMENTS

| | | |
|---|---|---|
| WO | WO94/16737 | 4/1994 |
| WO | 0102607 | 1/2001 |

OTHER PUBLICATIONS

Tobery et al., J. Ex. Med, 1997, 185(5):909-920.*
Haglund et al., J. Virol., 2002, 76(15):7506-7517.*
Gamvrellis et al., Immunology and Cell Biology, Sep. 28, 2004, 82:506-516.*
Pope, Current Molecular Medicine, 2003, 3:229-242.*
van Cauwenberge et al., Acta Otolaryngol (Stockh), 1996, 116: 316-321.*
Kim et al., Journal of Interferon and Cytokine Research, 2000, 20:487-498.*
Moore et al., Journal of Virology, 2002, 76(1):243-250.*
Uehara et al., The Journal of Immunology, 2002, 168:134-142.*
Bowman et al., Journal of Experimental Medicine, 2002, 195(2):269-275.*

(Continued)

*Primary Examiner* — Nicole Kinsey White
(74) *Attorney, Agent, or Firm* — Riverside Law LLP

(57) ABSTRACT

Compositions comprising one or more isolated nucleic acid molecules that encode an immunogen in combination with one or more of CTACK protein, TECK protein, MEC protein and functional fragments thereof and/or an isolated nucleic acid molecule that encodes a protein selected from the group consisting of: CTACK, TECK, MEC and functional fragments thereof are disclosed. Methods of inducing an immune response, including methods of inducing mucosal immune responses, in an individual against an immunogen, using such compositions are disclosed.

10 Claims, 7 Drawing Sheets

(56) References Cited

U.S. PATENT DOCUMENTS

| | | |
|---|---|---|
| 6,589,529 B1 | 7/2003 | Choi et al. |
| 7,338,794 B2 | 3/2008 | Gaertner et al. |
| 2003/0077247 A1 | 4/2003 | Caux et al. |
| 2003/0138413 A1 | 7/2003 | Vicari et al. |
| 2007/0087986 A1 | 4/2007 | Premack et al. |

OTHER PUBLICATIONS

Papadakis et al., The Journal of Immunology, 2003, 171:159-165.*
Natalizio et al., The Journal of Biological Chemistry, 2002, 277(45):42733-42740.*
Ramasamy et al., Biochimica et Biophysica Acta, 1999, 1453:1-13.*
Hruby, D.E., "Vaccinia virus vectors: new strategies for producing recombinant vaccines", Clinical Microbiology Reviews, 1990, 3(2):153-170.
Matthews, T.J. et al., "Prospects for development of a vaccine against HTLV-III-related disorders", AIDS Research and Human Retroviruses, 1987, 3(1):197-206.
Woodberry, T. et al., "Immunogenicity of a human immunodeficiency virus (HIV) polytope vaccine containing multiple HLA A2 HIV CD8(+) cytotoxic T-cell epitopes", Journal Virology, 1999, 73(7):5320-5325.
Campbell et al.,"Rapid Acquisition of Tissue-specific Homing Phenotypes by CD4+ T Cells Activated in Cutaneous or Mucosal Lymphoid Tissues," J. Exp. Med. (2002) 195:(1) 135-141.
Johansson-Lindbom et al., "Selective Generation of Gut Tropic T Cells in Gut-associated Lymphoid Tissue (GALT) : Requirement for GALT Dendritic Cells and Adjuvant," J. Exp. Med. (2003) 198:(6) 963-969.
Zabel et al., "Human G Protein-coupled Receptor GPR-9-6/CC Chemokine Receptor 9 Is Selectively Expressed on Intestinal Homing T Lymphocytes, Mucosal Lymphocytes, and Thymocytes and Is Required for Thymus-expressed Chemokine-mediated Chemotaxis," J. Exp. Med. (1999) 190:1241-1256.
Butcher et al., "Lymphocyte and Trafficking and Regional Immunity," Adv. Immunol (1999) 72:209-253.
Kunkel et al., "Lymphocyte CC Chemokine Receptor 9 and Epithelial Thymus-expressed Chemokine (TECK) Expression Distinguish the Small Intestinal Immune Compartment: Epithelial Expression of Tissue-specific Chemokines as an Organizing Principle in Regional Immunity," J. Exp. Med. (2000) 192:761-768.
Morales et. al., "CTACK, a skin-associated chemokine that preferentially attracts skin-horning memory T cells," Proc. Natl. Acad. Sci. U.S.A. (1998) 96:(25) 14470-14475.
Vicani, A.P., et al., "TECK: a novel cc chemokine specifically expressed by thymic dendritic cells and potentially involved in T cell development," Immunology (1997) 7:291-301.
Pan, J. et al., "A novel chemokine ligand for CCR10 and CCR3 expressed by epithelial cells in mucosal tissues," J. Immunol (2000) 165:(6) 2943-2949.
Howell, M.D., et al., "Limited T-cell receptor b-chain heterogenity among interleukin-2 receptor-positiv synovial T cells suggest a role for superantigen in rheumatoid arthritis," Proc. Nat. Acad. Sci. USA (1991) 88:10921-10925.
Paliard, X., et al., "Evidence for the effects of a superantigen in rheumatoid arthritis," Science (1991) 253:325-329.
Williams, W.V., et al., "Restricted heterogeneity of T cell receptor transcripts in rheumatoid synovium," J. Clin. Invest. (1992) 90:326-333.
Wucherpfennig, K.W., et al., "Shared human T cell receptor V beta usage to immunodominant regions of myelin basic protein," Science (1990) 246:1016-1019.
Oksenberg, J.R., et al., "Limited heterogeneity of rearranged T-cell receptor V alpha transcripts in brains of multiple sclerosis patients," Nature (1990) 345:344-346.
Chaudhary, V.K., et al., "A rapid method of cloning functional variable-region antibody genes in *Escherichia coil* as single-chain immunotoxins," Proc. Natl. Acad. Sci. USA (1990) 87:1066.

Jamin,D.I. et al., "Cutting edge: identification of the orphan receptor G-protein-coupled receptor 2 as CCR10, a specific receptor for the chemokine ESkine,", J. Immunol. (2000) 164:3460-3464.
Stenstad, H. et al., "Gut-associated lymphoid tissue-primed CD4+ T cells display CCR9-dependent and independent homing to the small intestine", Blood (2006) 107(9):3447-3454.
Svensson, M. et al., "Selective generation of gut-tropic T cells in gut-associated lymphoid tissues: requirement for GALT dendritic cells and adjuvant", Annals of the New York Academy of Sciences (2004) 1029:405-407.
Marsal, J. et al., "Involvement of CCL25 (TECK) in the generation of the murine small-intestinal CDBalpha+CD3+intraepithelial lymphocyte compartment", European Journal of Immunology (2002) 32(12) 3488-3497.
Williams, IR, "Chemokine receptors and leukocyte trafficking in the mucosal immune system", Immunologic Research (2004) 29(1-3):283-292.
Morales, J. et al., "CTACK, a skin-associated chemokine that preferentially attracts skin-homing memory T cells", Proceedings of the National Academy of Sciences of the United States of America (1999) 96(25):14470-14475.
Kunkel, EJ et al., "Chemokines and the tissue-specific migration of lymphocytes", Immunity (202) 16(1):1-4.
Kunkel, EJ et al., "Plasma-cell homing", Nature Reviews (2003) 3(10):822-829.
Kunkel, EJ et al., "CCR 10 expression is a common feature of circulating and mucosal epithelial tissue IgA Absecreting cells", The Journal of Clinical Investigation (2003) 111(7): 1001-10.
Kunkel, SL et al., "Cytokine phenotypes serve as a paradigms for experimental immune-mediated lung diseases and remodeling". American Journal of Respiratory Cell and Molecular Biology (2003) 29(3):S63-6.
Pan, J. et al., "A novel chemokine ligand for CCR10 and CCR3 expressed by epithelial cells in mucosal tissues", J. Immunol. (2000) 165(6)2943-2949.
Reiss, Y. et al., "CC Chemokine receptor (CCR) 4 and the CCR 10 ligand culaneous T cell-attracting chemokine (CTACK) in lymphocyte trafficking to inflamed skin", The Journal of Experimental Medicine, (2001) 194(10):1541-1547.
Soler. D. et al., "CCR4 versus CCR 10 in human cutaneous TH lymphocyte trafficking", Blood (2003) 101(5):1677-1682.
Hieshima, K. et al., "CC chemokine ligands 25 and 28 play essential roles in intestinal extravasation of IgA antibody-secreting cells", J Immunol. (2004) 173(6):3668-3675.
Lazarus, N.H. et al., "A common mucosal chemokine (mucosae-associated epithelial chemokine/CCL28) selectively attracts IgA plasmablasts", J. Immunol. (2003) 170(7):3799-3805.
Wang, W. et al., "Identification of a novel chemokine (CCL28), which binds CCR10 (GPR2)", The Journal of Biological Chemistry (2000) 275(29):22313-22323.
Nakayama, T. et al., "Cutting edge: profile of chemokine receptor expression on human plasma cells accounts for their efficient recruitment to target tissues", J. Immunol. (2003) 170(3):1136-1140.
Castelletti, E et al., "The Mucosae-Associated Epithelial Chemokine (MEC/CCL28) Modulates Immunity in HIV Infection", PloS ONE (2007) 2(10) e969.
Feng, N. et al.. "Redundant role of chemokines CCL25/TECK and CCL28/MEC in IgA+ plasmablast recruitment to the intestinal lamina propria after rotavirus infection", J. Immunol. (2006) 176(10):5749-5759.
Kutzler, M.A. et al., "Coimmunization with an optimized IL-I6 plasmid results in enhanced function and longevity of CD8 T cells that are partially independent of CD4 T cell help", J. Immunol. (2005) 175(1):112-123.
Eo, S.K. et al., "Immunopotentiation of DNA vaccine against herpes simplex virus via co-delivery of plasmid DNA expressing CCR7 ligands", Vaccines (2001) 19(32):4685-4693.
Biragyn, A. et al., "DNA vaccines encoding human immunodeficiency virus-1 glycoprotein 120 fusions with proinflammatory chemoattractants induce systemic and mucosal immune responses", Blood (2002) 100(4):1153-1159.
Okada, E. et al., "Intranasal immunization of a DNA vaccine with IL-12- and granulocyte-macrophage colony-stimulating factor

(56) References Cited

OTHER PUBLICATIONS (GM-CSF)-expressing plasmids in liposomes induces strong mucosal and cell-mediated immune responses against HIV-1 antigens", J. Immunol. (1997) 159(7):3638-3647.

Lee, S. et al., "Influence of DNA encoding cylokines on systemic and mucosal immunity following genetic vaccination against herpes simplex virus", Microbes Infect. (2003) 5(7):571-578.

Toka, F.N. et al., "Mucosal application of plasmid-encoded IL-15 sustains a highly protective anti-Herpes simplex virus immunity", J. Leukoc Biol. (2005) 78(1): 178-186.

Masopust, D. et al., "Cutting edge: gut microenvironment promotes differentiation of a unique memory CD8 T cell population", J. Immunol. (2006) 176(4):2079-2083.

Mora, J.R. et al., "Generation of gut-homing IgA-secreting B cells by intestinal dendritic cells", Science (2006) 314 (5802): 1157-1160.

Gao, J-Q et al., "Cotransduction of CCL27 gene can improve the efficacy and safety of 1L-12 gene therapy for cancer", Gene Therapy (2007) 14:491-502.

Gao, J-Q et al., "Antitumor Effect by Interleukin-11 Receptor α-Locus Chemokine/CCL27, Introduced into Tumor Cells through a Recombinant Adenovirus Vector", Cancer Research (2003) 63:4420-4425.

\* cited by examiner

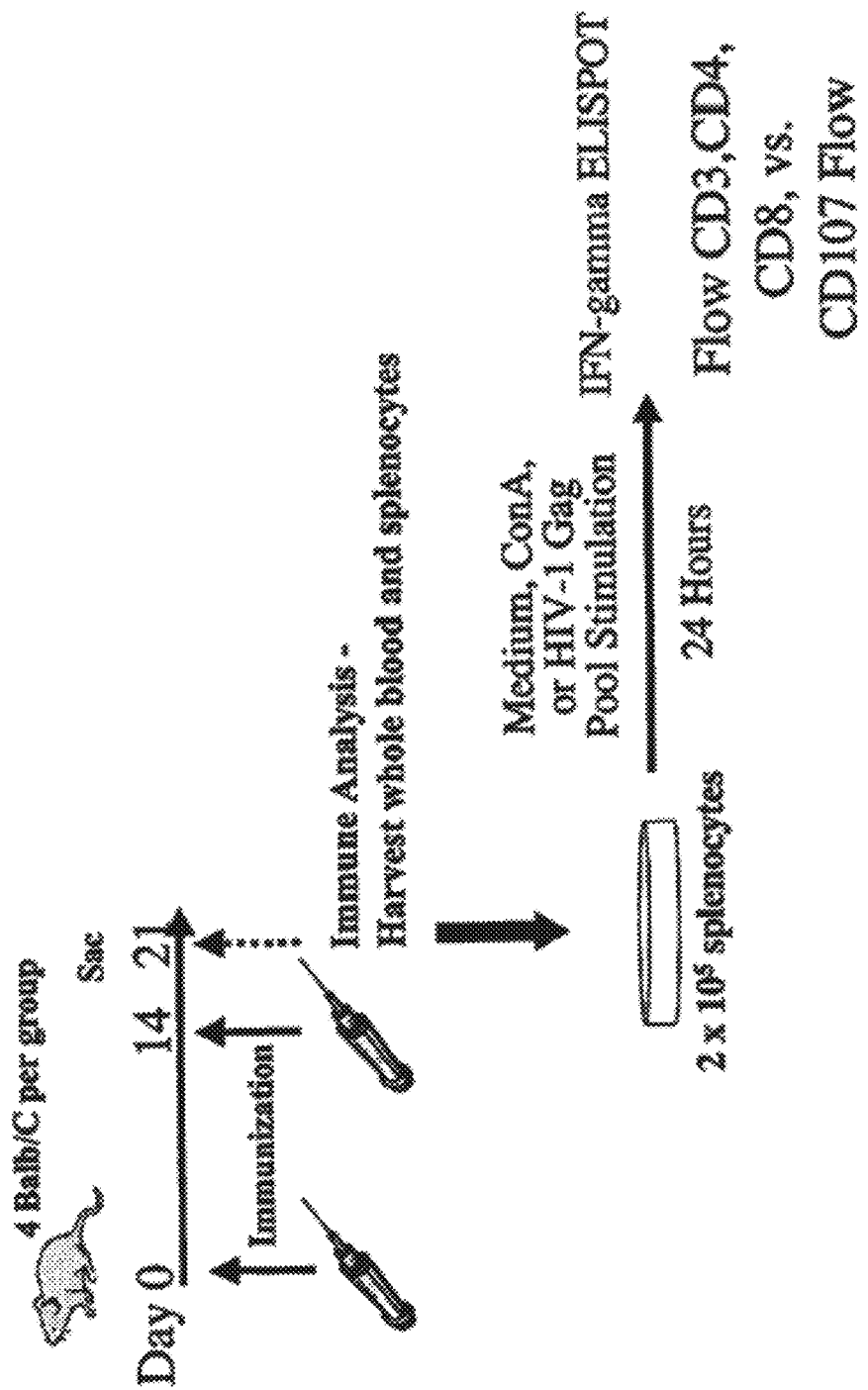

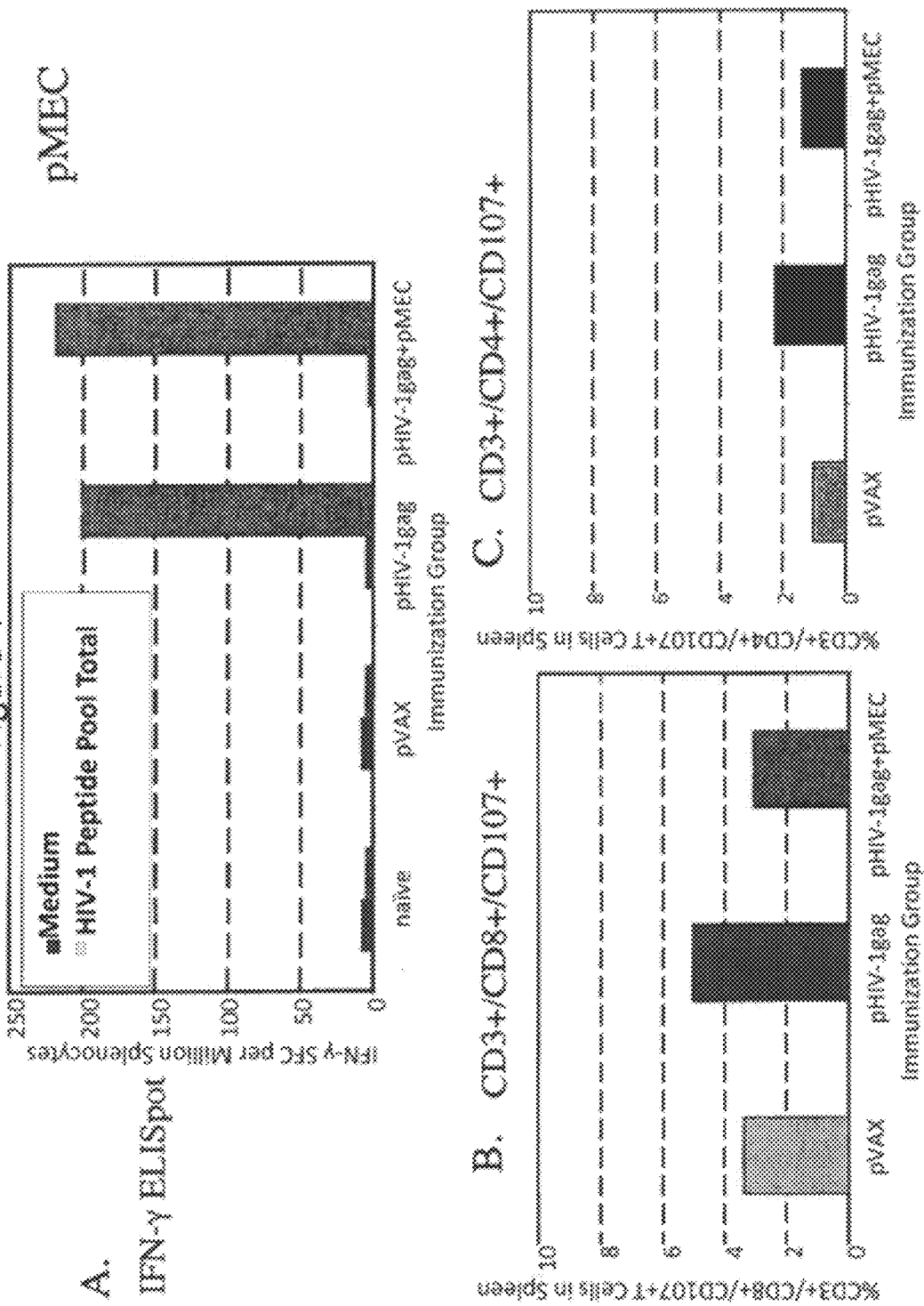

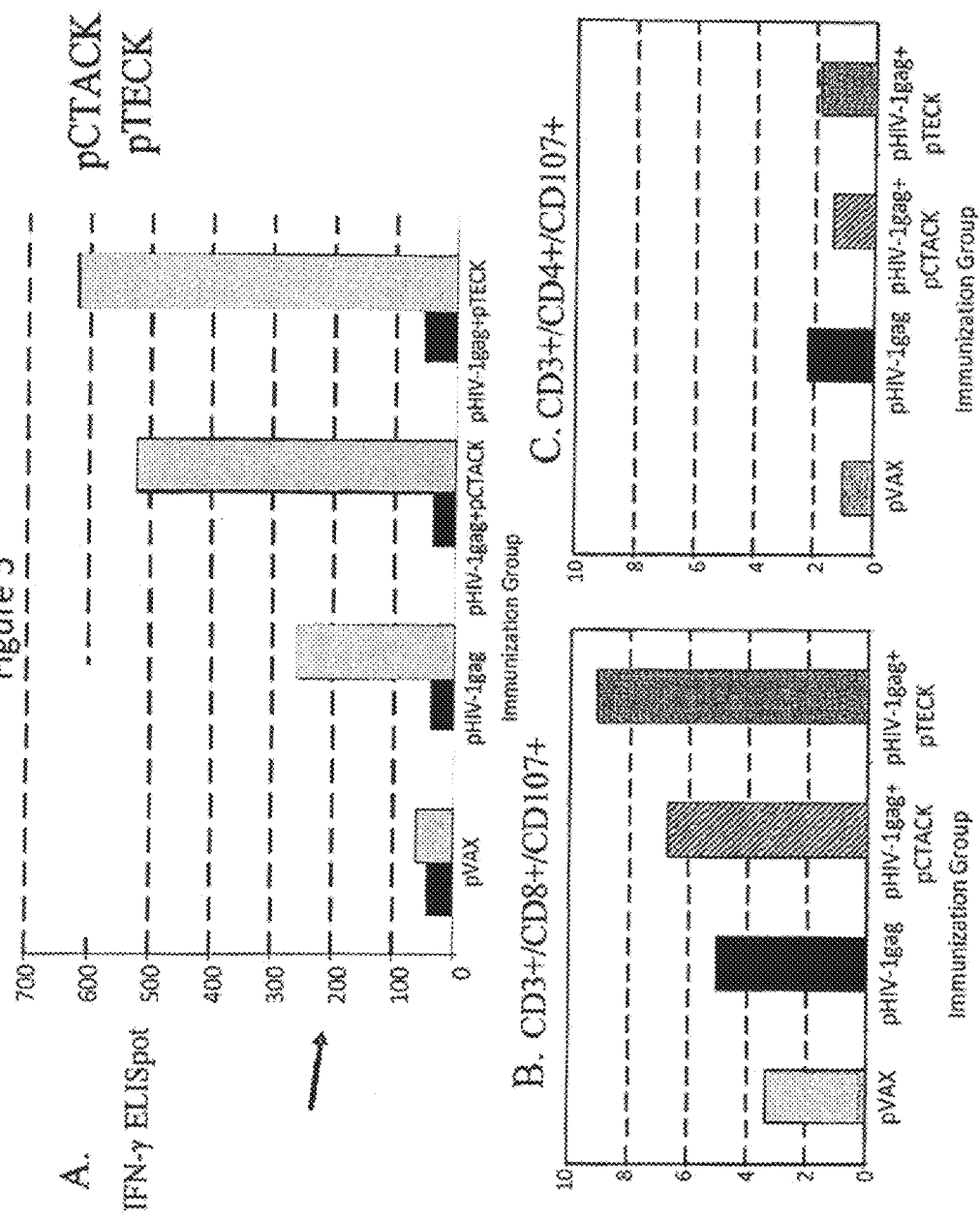

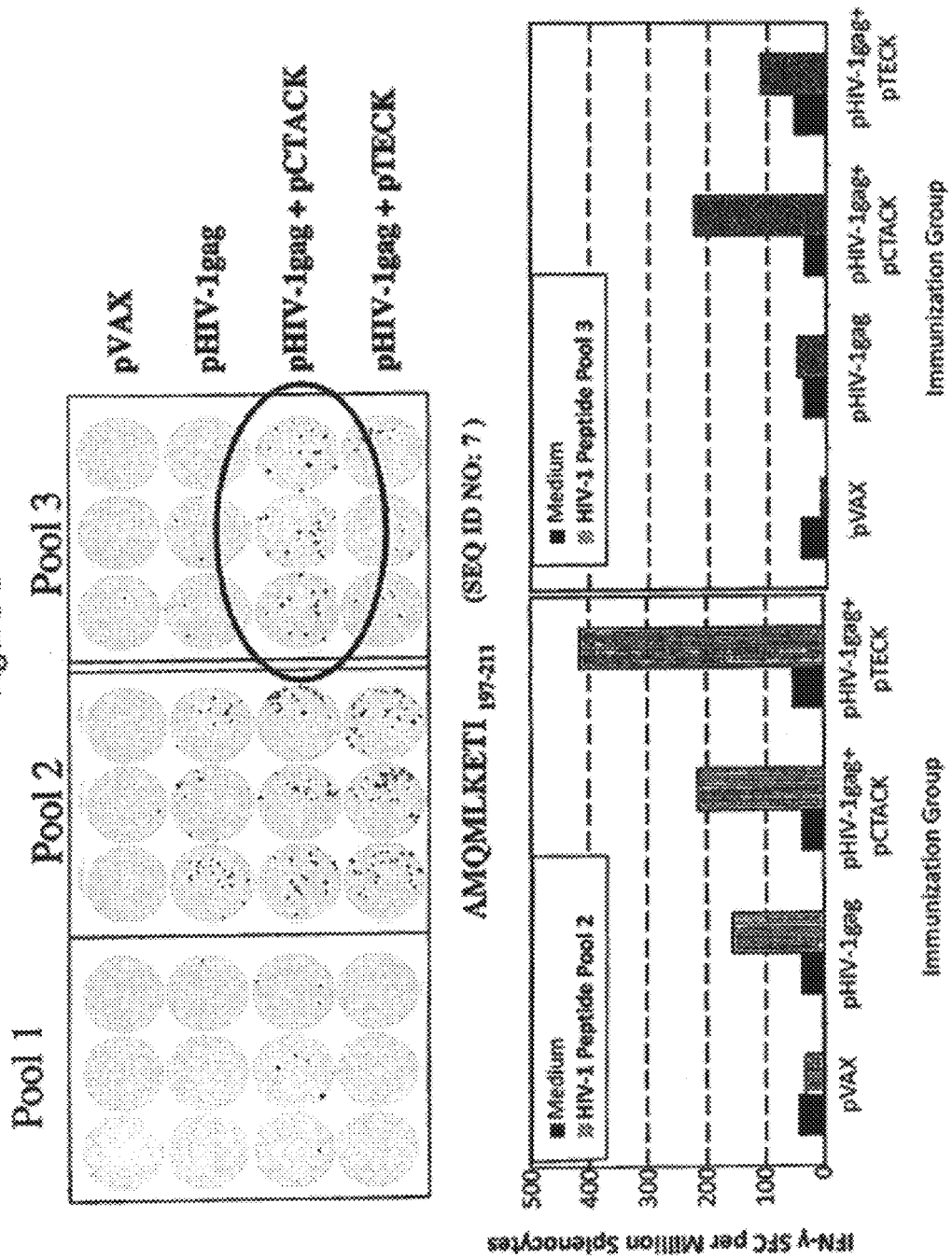

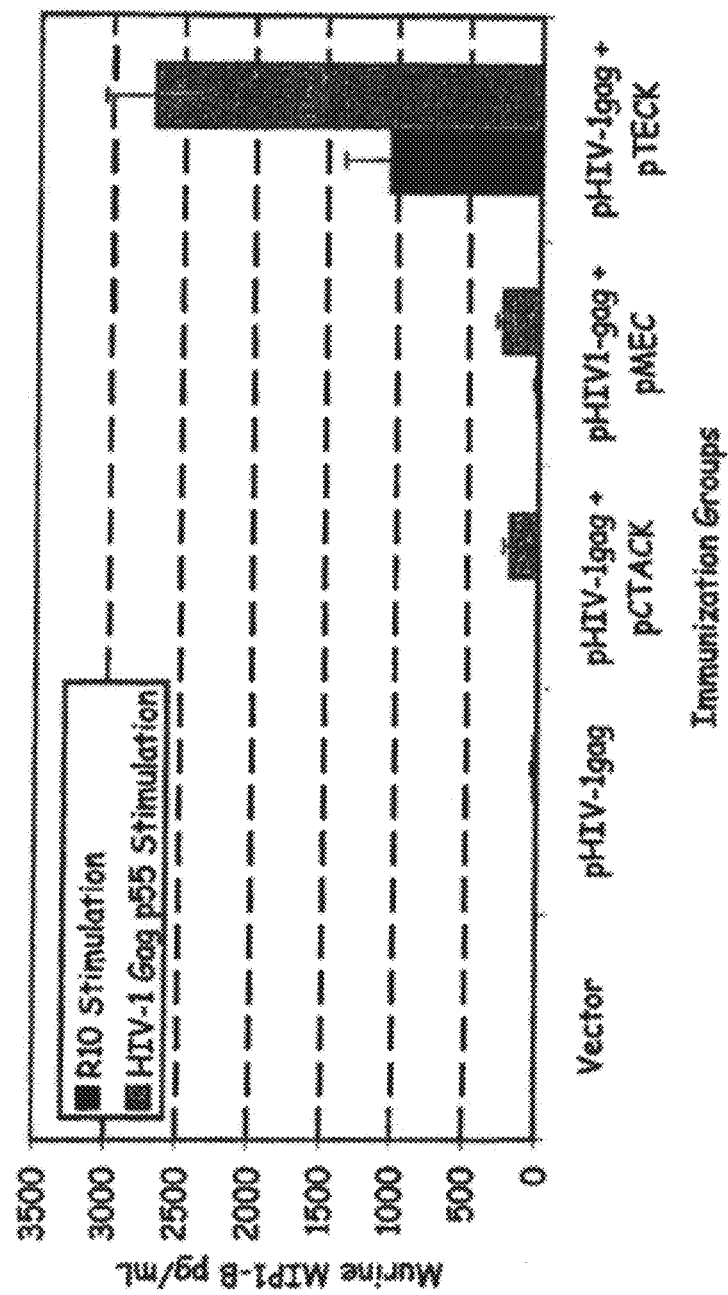

SEQUENCE LISTING

<160> NUMBER OF SEQ ID NOS: 7

<210> SEQ ID NO 1
<211> LENGTH: 377
<212> TYPE: DNA
<213> ORGANISM: Homo sapiens

<400> SEQUENCE: 1

```
atgaagggc ccccaacctt ctgcagcctc ctgctgctgt cattgctcct gagcccagac      60
cctacagcag cattcctact gccacccagc actgcctgct gtactcagct ctaccgaaag    120
ccactctcag acaagctact gaggaaggtc atccaggtgg aactgcagga ggctgacggg    180
gactgtcacc tccaggcttt cgtgcttcac ctggctcaac gcagcatctg catccacccc    240
cagaacccca gcctgtcaca gtggtttgag caccaagaga gaaagctcca tgggactctg    300
```
cccaagctga attttgggat gctaaggaaa atgggctgaa ccccccaata gccaaataat    360
aaagcagcat tggataa                                                   377

<210> SEQ ID NO 2
<211> LENGTH: 112
<212> TYPE: PRT
<213> ORGANISM: Homo sapiens

<400> SEQUENCE: 2

Met Lys Gly Pro Pro Thr Phe Cys Ser Leu Leu Leu Ser Leu Leu
1               5                   10                  15

Leu Ser Pro Asp Pro Thr Ala Ala Phe Leu Pro Pro Ser Thr Ala
                20                  25                  30

Cys Cys Thr Gln Leu Tyr Arg Lys Pro Leu Ser Asp Lys Leu Arg
            35                  40                  45

Lys Val Ile Gln Val Glu Leu Gln Glu Ala Asp Gly Asp Cys His Leu
        50                  55                  60

Gln Ala Phe Val Leu His Leu Ala Gln Arg Ser Ile Cys Ile His Pro
65                  70                  75                  80

Gln Asn Pro Ser Leu Ser Gln Trp Phe Glu His Gln Glu Arg Lys Leu
                85                  90                  95

His Gly Thr Leu Pro Lys Leu Asn Phe Gly Met Leu Arg Lys Met Gly
            100                 105                 110

<210> SEQ ID NO 3
<211> LENGTH: 879
<212> TYPE: DNA
<213> ORGANISM: Homo sapiens

<400> SEQUENCE: 3
atgaacctgt ggctcctggc ctgcctggtg ccggcttcc tgggagcctg ggccccgct     60 gtccacaccc aaggtgtctt tgaggactgc tgcctggcct accactaccc cattgggtgg   120
gctgtgctcc ggcgcgcctg gacttaccgg atccaggagg tgagcgggag ctgcaatctg   180
cctgctgcga tattctacct ccccaagaga cacaggaagg tgtgtgggaa ccccaaaagc   240
agggaggtgc agagagccat gaagctcctg gatgctcgaa ataaggtttt tgcaaagctc   300
caccacaaca tgcagacctt ccaagcaggc cctcatgctg taagaagtt gagttctgga   360 aactccaagt tatcatcatc caagtttagc aatcccatca gcagcagcaa gaggaatgtc   420
tccctcctga tatcagctaa ttcaggactg tgagccggct catttctggg ctccatcggc   480
acaggagggg ccggatcttt ctccgataaa accgtcgccc tacagaccca gctgtcccca   540
cgcctctgtc ttttgggtca agtcttaatc cctgcacctg agttggtcct ccctctgcac   600
ccccaccacc tcctgcccgt ctggcaactg gaaagaagga gttggcctga ttttaaccct   660
ttgccgctcc ggggaacagc acaatcctgg gcagccagtg gctcttgtag agaaaactta   720 ggataccctct ctcactttct gtttcttgcc gtccaccccg gccatgcca gtgtgtcctc   780 tgggtcccct ccaaaaatct ggtcattcaa ggatccccctc caaggctat gcttttctat   840 aacttttaaa taaaccttgg ggggtgaatg aataaaaaa                           879

<210> SEQ ID NO 4
<211> LENGTH: 150
<212> TYPE: PRT
<213> ORGANISM: Homo sapiens

<400> SEQUENCE: 4

```
Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Met Gln Thr Phe Gln Ala Gly Pro His
            100                 105                 110

Ala Val Lys Lys Leu Ser Ser Gly Asn Ser Lys Leu Ser Ser Ser Lys
            115                 120                 125

Phe Ser Asn Pro Ile Ser Ser Lys Arg Asn Val Ser Leu Leu Ile
            130                 135                 140

Ser Ala Asn Ser Gly Leu
145                 150

<210> SEQ ID NO 5
<211> LENGTH: 768
<212> TYPE: DNA
<213> ORGANISM: Homo sapiens

<400> SEQUENCE: 5
tgatcgaaca gcctcacttg tgttgctgtc agtgccagta gggcaggcag gaatgcagca    60
gagaggactc gccatcgtgg ccttggctgt ctgtgcggcc ctacatgcct cagaagccat   120
acttcccatt gcctccagct gttgcacgga ggtttcacat catatttcca gaaggctcct   180
ggaaagagtg aatatgtgtc gcatccagag agctgatggg gattgtgact tggctgctgt   240
catccttcat gtcaagcgca aagaatctg tgtcagcccg cacaaccata ctgttaagca   300
gtggatgaaa gtgcaagctg ccaagaaaaa tggtaaagga aatgtttgcc acaggaagaa   360
acaccatggc aagaggaaca gtaacagggc acatcagggg aaacacgaaa catacggcca   420
taaaactcct tattagagag tctacagata aatctacaga gacaattcct caagtggact   480
tggccatgat tggttgtcct gcatactgat gaaactactg atgtcagctg gtctgaagga   540
ccctaccaga agctaaatca tcaaagaatg caatttccat atcctaatga ttcaatctcc   600
cttaccctga ccaatcagtg gcccaaattt tccagcccct tgcctcccag aaccccagcc   660
cagaactctt cagagattta agaatctcct cctacctcct gactcagcac catgtaatca   720
ttaaactctc tgctgcaaaa aaaaaaaaaa aaaaaaaaa aaaaaaa                  768

<210> SEQ ID NO 6
<211> LENGTH: 127
<212> TYPE: PRT
<213> ORGANISM: Homo sapiens

<400> SEQUENCE: 6

Met Gln Gln Arg Gly Leu Ala Ile Val Ala Leu Ala Val Cys Ala Ala
1               5                   10                  15

Leu His Ala Ser Glu Ala Ile Leu Pro Ile Ala Ser Ser Cys Cys Thr
            20                  25                  30

Glu Val Ser His His Ile Ser Arg Arg Leu Leu Glu Arg Val Asn Met
```

```
                35                    40                    45
Cys Arg Ile Gln Arg Ala Asp Gly Asp Cys Asp Leu Ala Ala Val Ile
    50                    55                    60

Leu His Val Lys Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His His Gly Lys Arg Asn Ser Asn Arg
                100                 105                 110

Ala His Gln Gly Lys His Glu Thr Tyr Gly His Lys Thr Pro Tyr
            115                 120                 125

<210> SEQ ID NO 7
<211> LENGTH: 9
<212> TYPE: PRT
<213> ORGANISM: Artificial Sequence
<220> FEATURE:
<223> OTHER INFORMATION: HIV gag fragment 1

<400> SEQUENCE: 7

Ala Met Gln Met Leu Lys Glu Thr Ile
1               5
```

COMPOSITIONS FOR AND METHODS OF INDUCING MUCOSAL IMMUNE RESPONSES

This application is a divisional of U.S. patent application Ser. No. 11/719,646, filed Jun. 20, 2008, abandoned, which is a national stage of PCT International Application Serial Number PCT/US2005/042231, filed Nov. 18, 2005, which claims priority from U.S. Provisional Patent Application Ser. Nos. 60/629,737, filed Nov. 19, 2004 and 60/647,617, filed Jan. 27, 2005, each of which is incorporated herein by reference.

FIELD OF THE INVENTION

The present invention relates to improved vaccines, improved methods for inducing immune responses, including mucosal immune responses, and for prophylactically and/or therapeutically immunizing individuals against immunogens.

BACKGROUND OF THE INVENTION

Infectious agents commonly enter the host across a mucosal tissue such as the oral mucosa and other mucosa of the alimentary canal, the respiratory tract including olfactory and conjunctival mucosa, the mammary glands, and the genitourinary tract. The mucosal immune system provides a secretory immunoglobulin response to prevent infectious agents at these points of entry.

The secretory immune response includes clonal proliferation of antigen-specific B cells and progressive isotype switching by the B cell progeny to all subclasses of IgG- and IgA-secreting cells. Antigens such as microorganisms, proteins, polysaccharides, etc., that are encountered at a mucosal site can elicit local production of antibodies into the secretions that bathe the mucosal surface at the site, as well as other mucosal sites.

Secretory and circulating IgA production often exceeds that of other immunoglobulin isotypes. Secretory IgA as well as IgM and all subclasses of IgG have been found in virtually all external secretions, including tears, saliva, colostrum and milk, and in the mucous secretions of the respiratory, intestinal and genitourinary tracts.

The secretory IgA performs a protective role in the prevention of infectious diseases and for the inhibition of allergic reactions at mucosal surfaces. Secreted IgA neutralizes biologically active antigens, prevents uptake of antigens from the intestinal tract, and inhibits adherence of bacteria to epithelial surfaces.

Once antigen penetrates the mucosal epithelial cells, antigen-presenting cell-dependent activation of paracortical T cells and germinal center B cells within the Peyer's Patches is observed. However, the inductive stimuli required for differentiation of IgA-committed B cells is deferred until B cells have migrated through efferent lymphatics into the mesenteric lymph nodes after departure from the Peyer's Patches. Ultimately, IgA-committed, antigen-sensitized B cells enter the circulation through the lymph to populate various exocrine glands and mucosal epithelia throughout the body. Under local influences which include information provided by helper T cells, by the antigen and other biochemical mediators, terminal differentiation into IgA-secreting plasma cells occurs.

Tissue-selective trafficking of memory and effector T and B lymphocytes is mediated by a unique combination of adhesion molecules and chemokines Chemokines contribute to both lymphocytes exit from circulation and localization and retention within tissues. Memory T lymphocytes selectively re-circulate back through tissues including skin and intestines and other mucosal tissues. Chemokines and their receptors help control the movement of memory lymphocytes subsets through skin and gut. Effector T cells homing to the intestine and GALT express high levels of a4b7, whose ligand, MAdCAM-1 is expressed in the intestinal lamina propria and Peyers Patches. These mucosal T cells also express CCR9, whose ligand, TECK (CCL25) is selectively expressed by small intestinal epithelial cells. DC's which home to the mucosae express CCR10 which is the receptor for the chemokines Mec or c-TACK. (Campbell et al., J. Exp. Med. 2002, 195:(1) 135-141. Johansson-Lindbom et al., J. Exp. Med. 2003. 198(6), 963-969, which is incorporated herein by reference.)

Cutaneous lymphocyte-associated antigen (CLA+) memory T cells are preferentially targeted by CTACK and MEC. (Morales et al., 1999 PNAS, 96(25) 14470-14475, Jarmin et al., 2000 J. Immunol. 164:3460-3464). Therefore, CTACK, MEC and their receptors control movement of memory lymphocyte subsets in skin and gut.

Subset of circulating a4b7+ integrin lymphocytes from the small intestine co-express CCR9 and respond to TECK, and all T lymphocytes in the small intestinal epithelium express CCR9 (Zabel et al., 1999 J. Exp. Med. 190:1241-1256). Therefore, TECK and CCR9 play a critical role in lymphocyte biology in the mucosae.

Mucosal epithelia are major siteof secretory IgA by resident plasma cells. B cells secreting IgA also migrate preferentially to mucosae and express a4b7. B cells from spleen, MLN, and Peyer's patches express CCR9 (Butcher et al., 1999 Adv. Immunol. 72: 209-253, Kunkel et al., 2000 J. Exp. Med. 192:761-768). Therefore, TECK and CCR9 participate in localization of B cells that secrete IgA to mucosal sites.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce a humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

While such vaccines are often effective to immunize individuals prophylactically or therapeutically against pathogen infection or human diseases, there is a need for improved vaccines. There is a need for compositions and methods that produce an enhanced immune response.

Likewise, while some immunotherapeutics are useful to modulate immune response in a patient there remains a need for improved immunotherapeutic compositions and methods.

SUMMARY OF THE INVENTION

The present invention relates to a composition an isolated nucleic acid molecule that encodes an immunogen in combination with an isolated nucleic acid molecule that encodes one or more chemokines selected from the group consisting of: CTACK, TECK, MEC and functional fragments thereof.

The present invention further relates to a composition an isolated nucleic acid molecule that encodes both an immunogen and one or more chemokines selected from the group consisting of: CTACK, TECK, MEC and functional fragments thereof.

The present invention relates to injectable pharmaceutical compositions comprising an isolated nucleic acid molecule that encodes an immunogen in combination with an isolated nucleic acid molecule that encodes one or more chemokines selected from the group consisting of: CTACK, TECK, MEC and functional fragments thereof.

The present invention relates to injectable pharmaceutical compositions comprising an isolated nucleic acid molecule that encodes both an immunogen and one or more chemokines selected from the group consisting of: CTACK, TECK, MEC and functional fragments thereof.

The present invention further relates to methods of inducing an immune response in an individual against an immunogen, comprising administering to the individual a composition an isolated nucleic acid molecule that encodes an immunogen in combination with an isolated nucleic acid molecule that encodes one or more chemokines selected from the group consisting of: CTACK, TECK, MEC and functional fragments thereof.

The present invention further relates to methods of inducing an immune response in an individual against an immunogen, comprising administering to the individual a nucleic acid molecule that encodes an immunogen and one or more chemokines selected from the group consisting of: CTACK, TECK, MEC and functional fragments thereof.

The present invention further relates to methods of inducing a mucosal immune response in an individual against an immunogen, comprising administering to the individual a composition an isolated nucleic acid molecule that encodes an immunogen in combination with an isolated nucleic acid molecule that encodes one or more chemokines selected from the group consisting of: CTACK, TECK, MEC and functional fragments thereof.

The present invention further relates to methods of inducing a mucosal immune response in an individual against an immunogen, comprising administering to the individual a nucleic acid molecule that encodes an immunogen and one or more chemokines selected from the group consisting of: CTACK, TECK, MEC and functional fragments thereof.

The present invention further relates to recombinant vaccines comprising a nucleotide sequence that encodes an immunogen operably linked to regulatory elements, a nucleotide sequences that encode one or more chemokines selected from the group consisting of: CTACK, TECK, MEC and functional fragments thereof, and to methods of inducing an immune response, including methods of inducing a mucosal immune response, in an individual against an immunogen comprising administering such a recombinant vaccine to an individual.

The present invention further relates to a live attenuated pathogen comprising a nucleotide sequence that encodes one or more chemokines selected from the group consisting of: CTACK, TECK, MEC and functional fragments thereof, and to methods of inducing an immune response, including methods of inducing a mucosal immune response, in an individual against a pathogen comprising administering the live attenuated pathogen to an individual.

The present invention further relates to methods of inducing an immune response in an individual against an immunogen comprising administering to said individual one or more of CTACK protein, TECK protein, MEC protein and functional fragments thereof in combination with an isolated nucleic acid molecule that encodes an immunogen; and/or a recombinant vaccine that encodes an immunogen and/or a subunit vaccine that comprises an immunogen and/or a live attenuated vaccine and/or a killed vaccine.

A method of inducing an immune response in an individual against an immunogen comprising administering to said individual one or more of CTACK protein, TECK protein, MEC protein and functional fragments thereof in combination with an isolated nucleic acid molecule that encodes an immunogen; and/or a recombinant vaccine that encodes an immunogen and/or a subunit vaccine that comprises an immunogen and/or a live attenuated vaccine and/or a killed vaccine.

The present invention further relates to composition comprising: one or more of CTACK protein, TECK protein, MEC protein and functional fragments thereof in combination with one or more of an isolated nucleic acid molecule that encodes an immunogen; a recombinant vaccine comprising a nucleotide sequence that encodes an immunogen operably linked to regulatory elements; a live attenuated pathogen; and a killed pathogen.

The present invention further relates to methods of inducing an immune response in an individual against an immunogen comprising administering to said individual a composition comprising one or more of CTACK protein, TECK protein, MEC protein and functional fragments thereof in combination with an isolated nucleic acid molecule that encodes an immunogen; and/or a recombinant vaccine that encodes an immunogen and/or a subunit vaccine that comprises an immunogen and/or a live attenuated vaccine and/or a killed vaccine.

BRIEF DESCRIPTION OF THE FIGURES

FIG. 3 shows a depiction of the order of methodology employed.

FIG. 4 shows IFNγ ELISpot and Flow cytometry data comparing vector only, pHIV-1 gag only, and pHIV-1+ pMEC.

FIG. 5 shows IFNγ ELISpot and Flow cytometry data comparing vector only, pHIV-1 gag only, pHIV-1+pCTACK and pHIV-1+pTECK.

FIG. 6 shows IFNγ ELISpot data comparing vector only, pHIV-1 gag only, pHIV-1+pCTACK and pHIV-1+pTECK when stimulated with different HIV-1 Gag peptide pools.

FIG. 7 shows MIP1B expression data comparing vector only, pHIV-1 gag only, pHIV-1+pMEC, pHIV-1+pCTACK and pHIV-1+pTECK when stimulated with R10 or HIV-1 Gag.

DETAILED DESCRIPTION OF PREFERRED EMBODIMENTS

Figure 1:
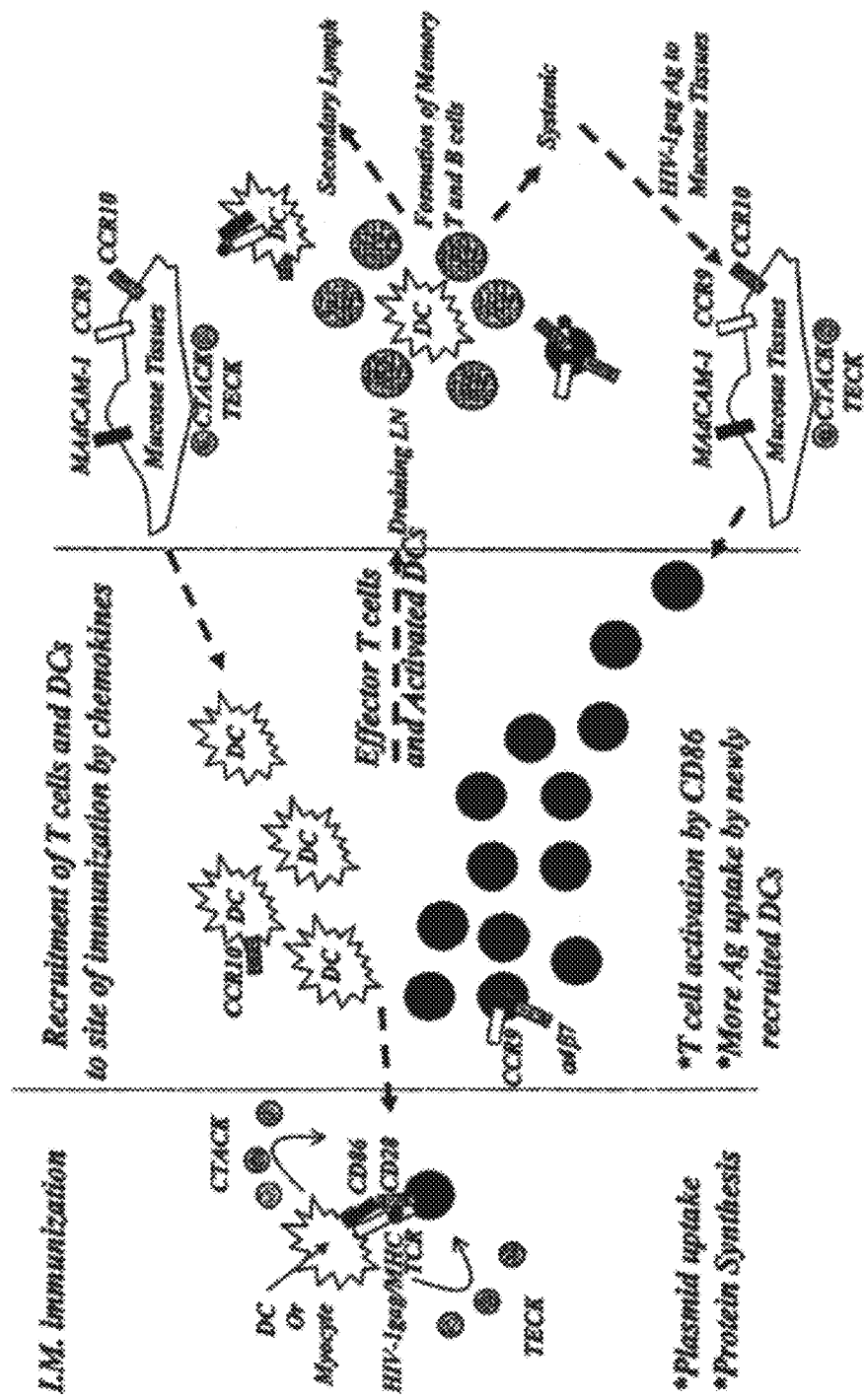
FIG. 1 depicts a proposed mechanism of plasmid induced cellular immune response in secondary lymphoid organs.

As used herein, "functional fragment" is meant to refer to a fragment of an immunomodulating protein that, when delivered in conjunction with an immunogen, provides an increased immune response compared to the immune that is induced when the immunogen is delivered without the fragment. Fragments are generally 10 or more amino acids in length.

As used herein the term "target protein" is meant to refer to peptides and protein encoded by gene constructs of the present invention that act as target proteins for a target protein-specific immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response that cross-reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease.

The invention arises from the discovery that when delivered in combination with an immunogen, each of the chemokines CTACK, TECK, MEC and functional fragments thereof, and combinations thereof modulates immune responses. Accordingly, a combination of these proteins may be delivered as components of a vaccine in order to induce a therapeutic or prophylactic immune response or in compositions useful to induce an immune response. In some embodiments, the means to deliver the immunogen is a DNA vaccine, a recombinant vaccine, a protein subunit vaccine, an attenuated vaccine or a killed vaccine. In some embodiments, the means to deliver one or more of CTACK, TECK, MEC and functional fragments thereof is by expression of coding sequences included in a DNA vaccine, a recombinant vaccine or an attenuated vaccine. In some embodiments, the means to deliver one or more of CTACK, TECK, MEC and functional fragments thereof is simply to administer the protein directly or to incorporate the protein as part of a recombinant vaccine, an attenuated vaccine or killed vaccine. In some embodiments, the means to deliver the immunogen is a DNA vaccine, a recombinant vaccine, a protein subunit vaccine, an attenuated vaccine or a killed vaccine and the one or more of CTACK, TECK, MEC and functional fragments thereof is by expression of coding sequences included in a DNA vaccine, a recombinant vaccine or an attenuated vaccine and/or by administering the protein directly and/or incorporated as part of a recombinant vaccine, an attenuated vaccine or killed vaccine.

Immune responses result in the production of antigen specific antibodies and/or antigen specific T- and B-cells. Antigen specific antibodies and/or cells provide the means to protect against infection, to reduce or to clear existing infection. They can also be isolated from the individual and used in other applications such as passive immunity protocols, immunocolumns or as reagents.

In some embodiments, CTACK, TECK and MEC are useful to induce mucosal immune responses, even in protocols where the composition is delivered systemically. In such embodiments, the presence of one or more of CTACK, TECK and MEC recruit mucosal immunity cells, such as dendritic cells from mucosae tissue, such as those expressing CCR10, or T cells from mucosae tissue, such as those expressing CCR9. These mucosal immunity cells become engaged in the immune response being generated against the co-expressed immunogen and result in the presence of primed effector T cells and activated dendritic cells at sites of mucosal tissue in the individual. Thus, systemic administration of vaccines that comprise one or more of the chemokines CTACK, TECK and MEC may be used to induce broad mucosal immunity.

CTACK, MEC and TECK play an important role in the recruitment of T and B lymphocytes and dendritic cells from the mucosae. CTACK, TECK and/or MEC are delivered as part of or in combination with various types of vaccines. The CTACK, TECK and/or MEC may be delivered as proteins as part or, as a single combination with and/or in combination with a DNA vaccine, recombinant viral vaccine, live, attenuated vaccine or killed vaccine. The CTACK, TECK and/or MEC may be delivered by delivering nucleic acid molecules which encode the proteins. These nucleic acid molecules may be incorporated within and/or delivered in a single composition with and/or delivered separately but in combination with a DNA vaccine, recombinant viral vaccine, live, attenuated vaccine or killed vaccine.

Co-immunization with an immunogen such as by DNA vaccine or other means plasmid plus one or more of these chemokines, such as in a DNA vaccine or part of the coding sequence of another type of vaccine, will provide a unique adjuvanting property by bringing mucosal relevant cells to the site of vaccination thus bringing mucosal relevant cells to the systemic immune system where the mucosal relevant cells can be primed by systemic DNA vaccine. FIG. 1 depicts a proposed mechanism of plasmid induced cellular immune response in secondary lymphoid organs. The plasmid or plasmids containing coding sequences for an immunogen and one or more of CTACK, TECK and MEC are delivered systemically to the individual such as by intramuscular injection in addition to the antigenic plasmid. The coding sequences are expressed by the plasmids in the myocyte and Dendritic cells that take up the plasmids. The secreted chemokine(s) recruit T cells and/or Dendritic cells including those from mucosal tissues which express the receptor for the chemokme. The recruited cells, which become antigen specific Effector T cells and activated Dendritic cells specific for the immunogen, migrate to the lymph system and mucosal sites, thereby providing a mucosal immune response and mucosal protection.

The GENBANK Accession number for the nucleotide sequence for murine (mouse) form of CTACK (CCL27) is accession number NM_011336, which is incorporated herein by reference. The GENBANK Accession number for the nucleotide sequence for human form of CTACK is accession number AF082393, which also references Morales, J., et al., CTACK, a skin-associated chemokine that preferentially attracts skin-homing memory T cells, Proc. Natl. Acad. Sci. U.S.A. 96 (25), 14470-14475 (1999) which are each incorporated herein by reference.

The nucleic acid sequence for the CTACK mRNA (SEQ ID NO:1) set forth in Genbank is:

```
                                              (SEQ ID NO: 1)
  1 atgaaggggc ccccaacctt ctgcagcctc ctgctgctgt
    cattgctcct gagcccagac 61 cctacagcag cattcctact gccacccagc actgcctgct
    gtactcagct ctaccgaaag 121 ccactctcag acaagctact gaggaaggtc atccaggtgg
    aactgcagga ggctgacggg 181 gactgtcacc tccaggcttt cgtgcttcac ctggctcaac
    gcagcatctg catccacccc 241 cagaacccca gcctgtcaca gtggtttgag caccaagaga
    gaaagctcca tgggactctg 301 cccaagctga attttgggat gctaaggaaa atgggctgaa
    gcccccaata gccaaataat 361 aaagcagcat tggataa
```

The CTACK mRNA translation product (SEQ ID NO:2) set forth in Genbank is:

```
                                              (SEQ ID NO: 2)
CTACK mRNA
MKGPPTFCSLLLLSLLLSPDPTAAFLLPPSTACCTQLYRKPLSDKLLRKV

IQVELQEADGDCHLQAFVLHLAQRSICIHPQNPSLSQWFEHQERKLHGTL

PKLNFGMLRKMG
```

CTACK is normally secreted from skin and interacts with the CCR10 which is normally produced in immature mucosal Dendretic cells.

The GENBANK Accession number for the nucleotide sequence for murine (mouse) form of TECK (CCL25) is accession number NM_009138, which is incorporated herein by reference. The GENBANK Accession number for the nucleotide sequence for human form of TECK is accession number HSU86358, which also references Vicari, A. P., et al., TECK: a novel cc chemokine specifically expressed by thymic dendritic cells and potentially involved in T cell development, Immunology 7, 291-301 (1997), which are each incorporated herein by reference.

The nucleic acid sequence for the TECK mRNA (SEQ ID NO:3) set forth in Genbank is:

```
                                              (SEQ ID NO: 3)
  1 atgaacctgt ggctcctggc ctgcctggtg
    gccggcttcc tgggagcctg ggcccccgct 61 gtccacaccc aaggtgtctt tgaggactgc
    tgcctggcct accactaccc cattgggtgg 121 gctgtgctcc ggcgcgcctg gacttaccgg
    atccaggagg tgagcgggag ctgcaatctg 181 cctgctgcga tattctacct ccccaagaga
    cacaggaagg tgtgtgggaa ccccaaaagc 241 agggaggtgc agagagccat gaagctcctg
    gatgctcgaa ataaggtttt tgcaaagctc 301 caccacaaca tgcagaccttc ccaagcaggc
    cctcatgctg taaagaagtt gagttctgga 361 aactccaagt tatcatcatc caagtttagc
    aatcccatca gcagcagcaa gaggaatgtc 421 tccctcctga tatcagctaa ttcaggactg
    tgagccggct catttctggg ctccatcggc 481 acaggagggg ccggatcttt ctccgataaa
    accgtcgccc tacagaccca gctgtcccca 541 cgcctctgtc ttttgggtca agtcttaatc
    cctgcacctg agttggtcct ccctctgcac 601 ccccaccacc tcctgcccgt ctggcaactg
    gaaagaagga gttggcctga ttttaacctt 661 ttgccgctcc ggggaacagc acaatcctgg
    gcagccagtg gctcttgtag agaaaactta 721 ggatacctct ctcactttct gtttcttgcc
    gtccaccccg ggccatgcca gtgtgtcctc 781 tgggtcccct ccaaaaatct ggtcattcaa
    ggatcccctc ccaaggctat gcttttctat 841 aacttttaaa taaaccttgg ggggtgaatg
    gaataaaaa
```

The TECK mRNA translation product (SEQ ID NO:4) set forth in Genbank is:

```
                                              (SEQ ID NO: 4)
TECK mRNA
MNLWLLACLVAGFLGAWAPAVHTQGVFEDCCLAYHYPIGWAVLRRAWTYR

IQEVSGSCNLPAAIFYLPKRHRKVCGNPKSREVQRAMKLLDARNKVFAKL

HHNMQTFQAGPHAVKKLSSGNSKLSSSKFSNPISSSKRNVSLLISANSGL
```

TECK is normally secreted in the colon, salivary gland, bronchi and mammary gland, and interacts with the CCR10 which is normally produced in immature mucosal Dendretic cells.

The GENBANK Accession number for the nucleotide sequence for murine (mouse) form of MEC (CCL28) is accession number NM_020279, which is incorporated herein by reference. The GENBANK Accession number for the nucleotide sequence for human form of MEC is accession number AF266504, which also references Pan, J. et al., A novel chemokine ligand for CCR10 and CCR3 expressed by epithelial cells in mucosal tissues, J. Immunol. 165 (6), 2943-2949 (2000), which are each incorporated herein by reference.

The nucleic acid sequence for the MEC mRNA (SEQ ID NO:5) set forth in Genbank is:

```
                                          (SEQ ID NO: 5)
  1 tgatcgaaca gcctcacttg tgttgctgtc agtgccagta
    gggcaggcag gaatgcagca 61 gagaggactc gccatcgtgg ccttggctgt ctgtgcggcc
    ctacatgcct cagaagccat 121 acttcccatt gcctccagct gttgcacgga ggtttcacat
    catatttcca gaaggctcct 181 ggaaagagtg aatatgtgtc gcatccagag agctgatggg
    gattgtgact tggctgctgt 241 catccttcat gtcaagcgca gaagaatctg tgtcagcccg
    cacaaccata ctgttaagca 301 gtggatgaaa gtgcaagctg ccaagaaaaa tggtaaagga
    aatgtttgcc acaggaagaa 361 acaccatggc aagaggaaca gtaacagggc acatcagggg
    aaacacgaaa catcggcca 421 taaaactcct tattagagag tctacagata aatctacaga
    gacaattcct caagtggact 481 tggccatgat tggttgtcct gcatactgat gaaactactg
    atgtcagctg gtctgaagga 541 ccctaccaga agctaaatca tcaaagaatg caatttccat
    atcctaatga ttcaatctcc 601 cttaccctga ccaatcagtg gcccaaattt tccagcccct
    tgcctcccag aaccccagcc 661 cagaactctt cagagattta agaatctcct cctacctcct
    gactcagcac catgtaatca 721 ttaaactctc tgctgcaaaa aaaaaaaaaa aaaaaaaaaa
    aaaaaaaa
```

The MEC mRNA translation product (SEQ ID NO:6) set forth in Genbank is:

```
                                          (SEQ ID NO: 6)
MEC mRNA
MQQRGLAIVALAVCAALHASEAILPIASSCCTEVSHHISRRLLERVNMC

RIQRADGDCDLAAVILHVKRRRICVSPHNHTVKQWMKVQAAKKNGKGNV

CHRKKHHGKRNSNRAHQGKHETYGHKTPY
```

MEC is normally secreted by epithelial cells in the small intestine and interacts with the CCR9 which is normally produced in mucosal Th1 and Th2 cells.

CTACK protein, TECK protein and MEC protein may each be isolated or produced routinely by those skilled in the art using well known techniques and readily available starting materials.

In some embodiments for which protein is used, for example, one having ordinary skill in the art can, using well known techniques, isolates any of CTACK protein, TECK protein and MEC protein from natural sources using, for example, immuno columns which contain antibodies that specifically bind to the protein. Alternatively, the protein may be separated using electrophoresis, isolated from the electrophoresis matrix and purified by for example dialysis to yield essentially pure protein. Other well known protein purification technologies can be employed to produce isolated, essentially pure protein.

In some embodiments for which protein is used, for example, one having ordinary skill in the art can, using well known techniques, inserts DNA molecules that encode any of CTACK protein, TECK protein, MEC protein and functional fragments thereof into a commercially available expression vector for use in well known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein from readily available starting materials. Such gene constructs are useful for the production of CTACK, TECK and MEC and functional fragments thereof. The expression vector including the DNA that encodes and of CTACK protein, TECK protein, MEC protein and functional fragments is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to isolating proteins from natural sources or producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production. According to some embodiments of the invention, the combination of an immunogen and one or more chemokines selected from the group consisting of: CTACK, TECK, MEC and functional fragments thereof is delivered to an individual to modulate the activity of the individual's immune system and thereby enhance the immune response against the immunogen. When the nucleic acid molecules that encode the chemokine(s) is taken up by cells of the individual the nucleotide sequences that encode the chemokine(s) is expressed in the cells and the proteins are thereby delivered to the individual. Aspects of the invention provide methods of delivering the coding sequences of the proteins on a single nucleic acid molecule, in compositions comprising different nucleic acid molecules that encodes one or more of the various chemokines, as part of recombinant vaccines and as part of attenuated vaccines.

According to some aspects of the present invention, compositions and methods are provided which prophylactically and/or therapeutically immunize an individual against an immunogen such as an allergen, a pathogen or abnormal, disease-related cells. The vaccine may be any type of vaccine such as, a live attenuated vaccine, a cell vaccine, a recombinant vaccine or a nucleic, acid or DNA vaccine. By delivering nucleic acid molecules that encode an immunogen and one or more chemokines selected from the group consisting of: CTACK, TECK, MEC and functional fragments thereof the immune response induced by the vaccine may be modulated. In particular, mucosal immune responses may be induced even if the composition is delivered to the individual by a non-mucosal route of delivery.

Isolated cDNA that encodes the chemokine proteins are useful as a starting material in the construction of constructs that can produce that chemokine protein. Using standard techniques and readily available starting materials, a nucleic acid molecule that encodes an chemokine protein may be prepared.

The present invention relates to compositions for delivering immunogens and chemokines Aspects of the present invention relate to nucleic acid molecules that comprise a nucleotide sequence that encodes one or more of CTACK, TECK, MEC and functional fragments thereof operably linked to regulatory elements in combination with a nucleotide sequence that encodes an immunogen operably linked to regulatory elements. Aspects of the present invention relate to compositions which comprise a nucleic acid molecule that comprises a nucleotide sequence that encodes one or more of CTACK, TECK, MEC and functional fragments thereof operably linked to regulatory elements in combination with a nucleic acid molecule that comprises a nucleotide sequence that encodes an immunogen operably linked to regulatory elements. Aspects of the present invention relate to compositions comprising one or more of CTACK protein, TECK protein, MEC protein and functional fragments thereof in combination with one or more of an isolated nucleic acid molecule that encodes an immunogen; a recombinant vaccine comprising a nucleotide sequence that encodes an immunogen operably linked to regulatory elements; a live attenuated pathogen; and a killed pathogen.

The present invention further relates to injectable pharmaceutical compositions that comprise such nucleic acid molecules and compositions.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, or "microprojectile bombardment gone guns".

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule.

Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operably linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct. In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Aspects of the present invention relate to compositions comprising one or more of CTACK protein, TECK protein, MEC protein and functional fragments thereof in combination with one or more of an isolated nucleic acid molecule that encodes an immunogen; a recombinant vaccine comprising a nucleotide sequence that encodes an immunogen operably linked to regulatory elements; a live attenuated pathogen; and a killed pathogen. In some embodiments, the composition comprises an isolated nucleic acid molecule that encodes an immunogen and/or a recombinant vaccine comprising a nucleotide sequence that encodes an immunogen operably linked to regulatory elements; wherein said immunogen is a pathogen antigen, a cancer-associated antigen or an antigen linked to cells associated with autoimmune diseases. In some embodiments, the immunogen is an HIV antigen such as HIV gag. In some embodiments, the composition further comprises a nucleic acid molecule that encodes one or more proteins of selected from the group consisting of: CTACK, TECK, MEC and functional fragments thereof is administered to the individual. In some embodiments, the composition is an injectable pharmaceutical composition.

According to some embodiments of the invention, methods of inducing immune responses, including methods of inducing mucosal immune responses, against an immunogen are provided by delivering a combination of the immunogen and one or more of CTACK, TECK, MEC and functional fragments thereof to an individual. The vaccine may be a live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof in combination with an isolated nucleic acid molecule that encodes an immunogen; and/or a recombinant vaccine that encodes an immunogen and/or a subunit vaccine that comprises an immunogen and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of: CTACK, TECK, MEC and functional fragments thereof is administered to the individual.

In some embodiments, the immunogen is a pathogen antigen, a cancer-associated antigen or an antigen linked to cells associated with autoimmune diseases. In some embodiments, the immunogen is an HIV antigen such as HIV gag.

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating proteins is introduced into the cells of tissue of an individual where it is expressed, thus producing the encoded proteins. The DNA or RNA sequences encoding the target protein and one or both immunomodulating proteins are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from the nucleic acid molecules that contain expressible forms of sequences that encode one or more immunomodulatory proteins. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode one or more of the immunomodulating proteins. Multiple different nucleic acid molecules can be produced and delivered according to the present invention and delivered to the individual. For example, in some embodiments, expressible forms of sequences that encode the target protein occur on separate nucleic acid molecule from the nucleic acid molecules that contain expressible forms of sequences that encode one or more of the two immunomodulating proteins which occur on separate nucleic acid molecule from the nucleic acid molecules that contain expressible forms of sequences that encode one or more immunomodulating proteins. In such cases, all three molecules are delivered to the individual.

The nucleic acid molecule(s) may be provided as plasmid DNA, the nucleic acid molecules of recombinant vectors or as part of the genetic material provided in an attenuated vaccine or cell vaccine. Alternatively, in some embodiments, the target protein and/or wither or both immunomodulating proteins maybe delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gene constructs that include one that comprises an expressible form of the nucleotide sequence that encodes a target protein and one that includes an expressible form of the nucleotide sequence that encodes an immunomodulating protein are provided. Incorporation into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, *listeria* and *shigella*. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material that encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HSV, HCV, WNV or HBV.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"—associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRP. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-1A and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include Vβ-3, Vβ-14, 20 Vβ-17 and Vα-17. Thus, vaccination with a DNA construct that encodes at least one of these proteins will elicit an immune response that will target T cells involved in RA. See: Howell, M. D., et al, 1991 *Proc. Nat. Acad. Sci. USA* 88:10921-10925; Piliard, X., et al, 1991 *Science* 253:325-329; Williams, W. V., et al, 1992 *J. Clin. Invest.* 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al, 1990 *Science* 248:1016-1019; Oksenberg, J. R., et al, 1990 *Nature* 345:344-346; each of which is incorporated herein by reference.

In scleroderma, several specific variable regions of TCRs that are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al., 1987 *Sequence of Proteins of Immunological Interest*, U.S. Department of Health and Human Services, Bethesda Md., which is incorporated herein by reference. In addition, a general method for cloning functional variable regions from antibodies can be found in Chaudhary, V. K., et al, 1990 *Proc. Natl. Acad. Sci. USA* 87:1066, which is incorporated herein by reference.

In addition to using expressible forms of immunomodulating protein coding sequence to improve genetic vaccines, the present invention relates to improved attenuated live vaccines, improved killed vaccines and improved vaccines that use recombinant vectors to deliver foreign genes that encode antigens as well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference. Gene constructs are provided which include the nucleotide sequence that encodes an immunomodulating protein is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include DNA vaccines, attenuated live vaccines and recombinant vaccines. The gene constructs comprise a nucleotide sequence that encodes an immunomodulating protein and that is operably linked to regulatory sequences that can function in the vaccine to effect expression. The improved vaccines result in an enhanced cellular immune response. In some embodiments, the CTAC, TECK, MEC or functional fragment thereof may be included as a protein in combination with or part of the viral composition or delivered separately. In some embodiments, one or more of the CTAC, TECK, MEC or functional fragment thereof is part of the structure of the vaccine protein, vaccine glycoprotein vaccine vector or attenuated or killed pathogen. For example, fusion proteins comprising the CTAC, TECK, MEC or functional fragment may be part of the structural proteins that make up the virus, organism or part of a fusion protein that may include the glycoprotein or protein subunit. In other examples, the CTAC, TECK, MEC or functional fragment is an intact protein which is complexed with DNA vaccine, glycoprotein or protein subunit or part of the viral vector or organism. In some embodiments, compositions comprise one or more of the CTAC, TECK, MEC or functional fragment thereof is a protein which is part of the structure of the vaccine vector or attenuated or killed pathogen. In some embodiments, compositions are provided in which the one or more CTAC, TECK, MEC or functional fragment thereof is combined with a DNA vaccine, glycoprotein or protein subunit or part of the viral vector or organism. In some embodiments, nucleic acid molecules encoding the one or more CTAC, TECK, MEC or functional fragment thereof is combined with a DNA vaccine, glycoprotein or protein subunit or part of the viral vector or organism. In some embodiments, nucleic acid molecules encoding the one or more CTAC, TECK, MEC or functional fragment thereof is a portion of a DNA vaccine, or part of the genome of a viral vector or organism.

Example

Figure 2:
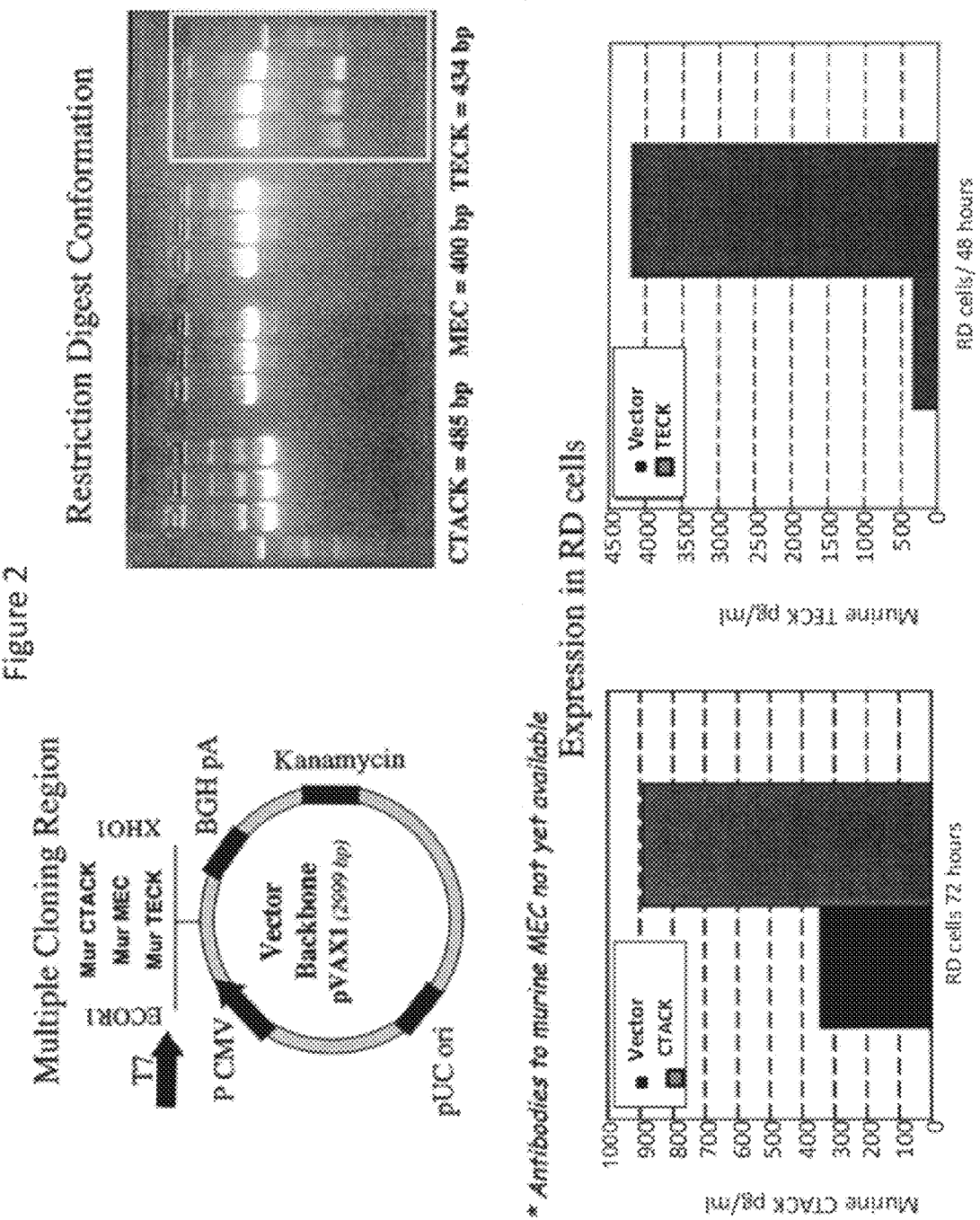
FIG. 2 shows construction of plasmids used in the Example and data confirming the identity and expression of the chemokine coding sequences.

Plasmids were constructed using the pVax1 (Invitrogen) backbone, inserting coding sequences for murine CTACK, murine TECK or murine MEC into the multiple cloning region of pVax1, placing the coding sequences under the regulatory control of the cytomegalovirus promoter and bovine growth hormone polyadenylation signal. (FIG. 2) Inserts were confirmed by restriction digest conformation (FIG. 2). RD cells were transfected with vector or construct (pCTACK or pTECK) to confirm that the coding sequences would be expressed. Testing was not done to confirm pMEC expression as antibodies against murine MEC were not available. The data shown in FIG. 2 confirms that CTACK and TECK was expressed.

Balb/C mice (N=4 per group) were immunized with vector only, plasmid pHIV-1gag only (pVax-1 with HIV-1 gag inserted at multiple cloning site), plasmid pHIV-1gag+pCTACK, plasmid pHIV-1gag+pTECK and plasmid pHIV-1gag+pMEC on days 0 and 14. Mice were sacrificed at day 21 and spleens were removed for immune analysis (FIG. 3). Plates containing 2×10$^5$ splenocytes in triplicate were incubated with medium only, medium+concavalin A or medium+pools of Gag peptides. Pools of Gag peptide contained 15 amino acid fragments of Gag each having 11 amino acid overlap with another peptide in the pool. Pools were divided into three groups spanning the 122 amino acid length of gag.

ELISpot testing was done to measure IFNγ production from cells from naive, vector only, plasmid pHIV-1gag only (pVax-1 with HIV-1 gag inserted at multiple cloning site), plasmid pHIV-1gag+pCTACK, plasmid pHIV-1gag+pTECK and plasmid pHIV-1gag+pMEC that were exposed to HIV-1 Gag peptide pool. Production of IFNγ in response to Gag indicates that the cells activated by Gag in an antigen specific manner.

Flow cytometry was performed on cells from naive, vector only, plasmid pHIV-1gag only (pVax-1 with HIV-1gag inserted at multiple cloning site), plasmid pHIV-1gag+pCTACK, plasmid pHIV-1gag+pTECK and plasmid pHIV-1gag+pMEC that were exposed to HIV-1Gag peptide pool staining for the markers CD3+, CD8+, CD4+ and GD107+. CD3+ selects for T cells. Most CTLs are CD8+ although some may be CD4+. CD 107+ (also referred to as Lamp-1) is a marker for antigen specific activated CTLs.

FIG. 4 shows data for MEC. IFNγ ELISpot data shows a small increase in IFNγ spots. No increase was observed in CD3+/CD8+/CD107+ and CD3+/CD4+/CD107+ although it is not clear whether this was due to a lack of expression of MEC, insufficient expression or a lack of activity.

FIG. 5 shows data for CTACK and TECK. IFNγ ELISpot data shows a significant increase in IFNγ spots in groups which included pCTACK or pTECK. Results from CD3+/CD8+/CD107+ show a significant increase in percent positive populations in groups which included pCTACK or pTECK. No increase was seen in CD3+/CD4+/CD107+ data.

TECK, which is a chemokine that attracts T cells from the mucosal environment, is the most potent driver of CD8 CTL responses among the selected set of mucosal relevant chemokines tested. However CTACK, a chemokine which should attract DC of mucosal origin, is very interesting as well. As shown in FIG. 6, IFNγ ELISpot data using different pools show that C-TACK is stimulated by one or more peptides in pool 3 as well as pool 2. TECK shows stimulation by one or more Gag peptides in pool 2 which is consistent with data from pHIV-1gag only as well as observations seen elsewhere. The presence of CTACK appeared to render the cells stimulated by an additional, different epitope.

MIP1B ELISA were done to determine if MIP1B would be produced when cells from the various groups are stimulated by R10 or HIV-1gag p55. FIG. 7 shows that in response to stimulation by Gag p55 MIP1B is produced by cells from each of the groups pHIV-1gag+pCTACK, pHIV-1gag+pTECK, and pHIV-1gag+pMEC relative to that produced by the control groups pHIV-1gag only or pVax1 only. The amount of MIP1B produced in by cells from the pHIV-1gag+pTECK group was significantly greater than the amount produced by either the pHIV-1gag+pCTACK group or the pHIV-1gag+pMEC group.

TABLE 1

| Picornavirus Family | |
| --- | --- |
| Genera: | Rhino viruses: (Medical) responsible for - 50% cases of the common cold.<br>Etheroviruses: (Medical) includes polioviruses, coxsackieviruses, echoviruses, and human enteroviruses such as hepatitis A virus.<br>Apthoviruses: (Veterinary) these are the foot and mouth disease viruses.<br>Target antigens: VP1, VP2, VP3, VP4, VPG |
| Calciviras Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Senilis viruses, RossRiver virus and Eastern & Western, Equine encephalitis.<br>Reovirus: (Medical) Rubella virus. |
| Flariviridue Family | Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |

TABLE 1-continued

| | |
|---|---|
| | Representative Target antigens:<br>E 35<br>NS5<br>C<br>Hepatitis C Virus: (Medical) these viruses are not placed in a<br>family yet but are believed to be either a togavirus or a<br>flavivirus. Most similarity is with togavirus family. |
| Coronavirus Family:<br>(Medical and Veterinary) | |
| Genera: | Infectious bronchitis virus (poultry)<br>Porcine transmissible gastroenteric virus (pig)<br>Porcine hemaglutinating encephalomyelitis virus (pig)<br>Feline infectious peritonitis virus (cats)<br>Feline enteric coronavirus (cat)<br>Canine coronavirus (dog)<br>SARS associated coronavirus<br>The human respiratory coronaviruses cause ~40 cases of<br>common cold. EX. 224E, OC43<br>Note - coronaviruses may cause non-A, B or C hepatitis<br>Target antigens:<br>E1 - also called M or matrix protein<br>E2 - also called S or Spike protein<br>E3 - also called BE or hemagglutin-elterose<br>glycoprotein (not present in all coronaviruses)<br>N - nucleocapsid |
| Rhabdovirus Family Genera: | |
| Genera: | Vesiliovirus<br>Lyssavirus: (medical and veterinary)<br>rabies<br>Target antigen:<br>G protein<br>N protein |
| Filoviridue Family: (Medical) | |
| | Hemorrhagic fever viruses such as Marburg and Ebola virus |
| Paramyxovirus Family: | |
| Genera: | Paramyxovirus: (Medical and Veterinary)<br>Mumps virus, New Castle disease virus (important pathogen<br>in chickens)<br>Morbillivirus: (Medical and Veterinary)<br>Measles, canine distemper<br>Pneuminvirus: (Medical and Veterinary)<br>Respiratory syncytial virus |
| Orthomyxovirus Family (Medical)<br>Bungavirus Family | The Influenza virus |
| Genera: | Bungavirus: (Medical) California encephalitis, LA Crosse<br>Phlebovirus: (Medical) Rift Valley Fever<br>Hantavirus: Puremala is a hemahagin fever virus Nairvirus<br>(Veterinary) Nairobi sheep disease<br>Also many unassigned bungaviruses |
| Arenavirus Family (Medical)<br>Reovirus Family | LCM, Lassi fever virus |
| Genera: | Reovirus: a possible human pathogen<br>Rotavirus: acute gastroenteritis in children<br>Orbiviruses: (Medical and Veterinary) Colorado Tick fever,<br>Lebombo (humans) equine encephalosis, blue tongue |
| Retrovirus Family<br>Sub-Family: | |
| Genera: | Oncorivirinal: (Veterinary) (Medical) feline leukemia virus,<br>HTLVI and HTLVII<br>Lentivirinal: (Medical and Veterinary) HIV, feline<br>immunodeficiency virus, equine infections, anemia virus<br>Spumavirinal |
| Papovavirus Family | |
| Sub-Family:<br>Sub-Family: | Polyomaviruses: (Medical) BKU and JCU viruses<br>Papillomavirus: (Medical) many viral types associated with<br>cancers or malignant progression of papilloma.<br>Adenovirus (Medical)<br>EX AD7, ARD., O.B. - cause respiratory disease - some<br>adenoviruses such as 275 cause enteritis |
| Parvovirus Family (Veterinary) | Feline parvovirus: causes feline enteritis<br>Feline panleucopeniavirus |

TABLE 1-continued

| | |
|---|---|
| | Canine parvovirus |
| | Porcine parvovirus |
| Herpesvirus Family | |
| Sub-Family: | alphaherpesviridue |
| Genera: | Simplexvirus (Medical) |
| | HSVI (GenbankX14112, NC001806), HSVII (NC001798) |
| | Varicellovinis: (Medical Veterinary) pseudorabies - |
| | varicella zoster |
| Sub-Family - betaherpesviridue | |
| Genera: | Cytomegalovirus (Medical) |
| | HCMV |
| | Muromegalo virus |
| Sub-Family. Gammaherpesviridue | |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Variola. (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxviru's |
| Sub-Family: | Entemopoxviridue |
| Hepadnavirus Family | Hepatitis B virus |
| | Unclassified |
| | Hepatitis delta virus |

TABLE 2

Bacterial pathogens

Pathogenic gram-positive cocci include: pneumococcal; staphylococcal; and streptococcal.
Pathogenic gram-negative cocci include: meningococcal; and gonococcal.
Pathogenic enteric gram-negative bacilli include: enterobacteriaceae; pseudomonas, acinetobacteria and eikenella, melioidosis;, sahnonella; shigellosis; hemophilus; chancroid; brucellosis; tularemia; yersinia (pasteurella); streptobacillus mortiliformis and spirillum; listeria monocytogenes; erysipelothrix rhusiopathiae; diphtheria, cholera, anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; - treponematoses: yaws, pinta and endemic syphilis; and leptospirosis.

TABLE 2-continued

Other infections caused by higher pathogen bacteria and pathogenic fungi include: actinomycosis;. nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis.
Rickettsial infections include rickettsial and rickettsioses.
Examples of mycoplasma and chlarnydial infections include: mycoplasma pneumoniae; lymphogranuloma venereum; psittacosis; and perinatal chlamydial infections.
Pathogenic eukaryotes
Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

The invention claimed is:

1. A composition consisting of:
   an isolated nucleic acid molecule that comprises a nucleic acid sequence that encodes an immunogen operably linked to regulatory elements that are functional in a human, wherein said immunogen is a pathogen antigen from a pathogen that enters a human host across mucosal tissue that is selected from the group consisting of: oral mucosa, other alimentary canal mucosa, olfactory mucosa, conjunctival mucosa, other respiratory tract mucosa, mucosa of mammary glands, and genitourinary tract mucosa; and
   an isolated nucleic acid molecule that comprises a nucleic acid sequence that encodes TECK, wherein said nucleic acid sequence that encodes TECK is operably linked to regulatory elements that are functional in a human,
   wherein said nucleic acid molecules are plasmids, further wherein said plasmids are constructed by inserting said coding sequences into the multiple cloning region of a pVax1 backbone, wherein said coding sequences are under the regulatory control of the cytomegalovirus promoter and bovine growth hormone polyadenylation signal.

2. The composition of claim 1 wherein said immunogen is an HIV antigen.

3. The composition of claim 2 wherein said HIV antigen is gag.

4. A composition consisting of an isolated nucleic acid molecule that comprises a nucleotide sequence that encodes an immunogen operably linked to regulatory elements that are functional in a human, wherein said immunogen is a pathogen antigen from a pathogen that enters a human host across mucosal tissue that is selected from the group consisting of: oral mucosa, other alimentary canal mucosa, olfactory mucosa, conjunctival mucosa, other respiratory tract mucosa, mucosa of mammary glands, and genitourinary tract mucosa and
   a nucleotide sequence that encodes TECK, wherein said nucleic acid sequence that encodes TECK is operably linked to regulatory elements that are functional in a human,
   wherein said nucleic acid molecule is a plasmid, further wherein said plasmid is constructed by inserting said coding sequences into the multiple cloning region of a pVax1 backbone, wherein said coding sequences are under the regulatory control of the cytomegalovirus promoter and bovine growth hormone polyadenylation signal.

5. The composition of claim 4 wherein said immunogen is an HIV antigen.

6. The composition of claim 5 wherein said HIV antigen is gag.

7. An injectable pharmaceutical composition comprising the composition of claim 1.

8. An injectable pharmaceutical composition comprising the composition of claim 4.

9. The composition of claim 1 wherein said immunogen is a viral antigen.

10. The composition of claim 4 wherein said immunogen is a viral antigen.

* * * * *